United States Patent [19]

Goodfellow et al.

[11] Patent Number: 5,610,140
[45] Date of Patent: Mar. 11, 1997

[54] BRADYKININ RECEPTOR ANTAGONISTS WITH NEUROKININ RECEPTOR BLOCKING ACTIVITY

[75] Inventors: Val S. Goodfellow, Westminster; Eric T. Whalley, Golden; Francine E. Wincott, Longmont, all of Colo.

[73] Assignee: Cortech, Inc., Denver, Colo.

[21] Appl. No.: 284,068

[22] Filed: Aug. 1, 1994

Related U.S. Application Data

[63] Continuation-in-part of Ser. No. 974,000, Nov. 10, 1992, abandoned, which is a continuation-in-part of Ser. No. 859,582, Mar. 27, 1992, abandoned, which is a continuation-in-part of Ser. No. 677,391, Apr. 1, 1991, abandoned.

[51] Int. Cl.⁶ ............................. A61K 38/08; C07K 7/18
[52] U.S. Cl. .................... 514/15; 514/12; 514/2; 530/314; 530/328; 530/402; 530/408; 530/807; 530/816; 530/815; 548/361.1; 435/107; 435/118; 435/121; 435/117; 435/129; 435/128
[58] Field of Search ................... 514/15, 12, 2; 530/314, 328, 402, 408, 807, 816, 815; 548/310; 435/107, 118, 121, 117, 129, 128

[56] References Cited

U.S. PATENT DOCUMENTS

| | | |
|---|---|---|
| 4,618,598 | 10/1986 | Conn . |
| 4,894,443 | 1/1990 | Greenfield ........................ 530/388 |
| 5,164,372 | 11/1992 | Matsuo et al. ................... 514/19 |

FOREIGN PATENT DOCUMENTS

| | | | |
|---|---|---|---|
| 0333174A2 | 9/1989 | European Pat. Off. | C07K 5/00 |
| 0394989A2 | 10/1990 | European Pat. Off. | C07K 5/00 |
| 0443132A1 | 8/1991 | European Pat. Off. | C07K 5/06 |
| WO89/01781 | 3/1989 | WIPO . | |
| WO92/22569 | 12/1992 | WIPO | C07K 5/06 |

OTHER PUBLICATIONS

Cheronis et al, Recent Progress on Kinins, pp. 551–558, (1992).
Stewart et al, Advances in Expt'l. Med. and Biology, pp. 185–589 (1983).
Vavrek et al, Peptide, Struct. and Funct. Proceedings of the 8th Am. Pept. Symp. (1983), pp. 381–384.
Kodama et al, European Journal of Pharmacology, vol. 151, pp. 317–320 (1988).
Calixto, et al., "Nonpeptide Bradykinin Antagonists," pp. 97–129 (1991).
Carr, "The Effect of Anti–Inflammatory Drugs on Increased Vascular Permeability Induced by Chemical Mediators," *J. Pathology*, 108, 1–14 (1972).
Cheronis, et al. "Bradykinin Antagonists: Synthesis and In Vitro Activity of Bissuccinimidoalkane Peptide Dimers," In: *Recent Progress in Kinins*, pp. 551–558 (1992).
Christopher, T. A., et al., "Beneficial Actions of CP–0127, a Novel Bradykinin Receptor Antagonist, in Murine Traumatic Shock," *Am. J. Physiol.*, 266, H867–H873 (1994).
Desai, M. C., et al., "Discovery of a Potent Substance P Antagonist: Recognition of the Key Molecular Determinant," *J. Med. Chem.*, 35, 4911–4913 (1992).
Hagiwara, D., et al., "Studies on Neurokinin Antagonists. 2. Design and Structure–Activity Relationships of Novel Tripeptide Substance P Antagonists, $N^{\alpha}$–[$N^{\alpha}$–($N^{\alpha}$–Acetyl–L–Threonyl)–$N^{1}$–Formyl–D–Tryptophyl]–N–methyl–N–(phenyl–methyl)–L–phenylalaninamide and Its Related Compounds," *J. Med. Chem.*, 35, 3184–3191 (1992).
Hagiwara, D., et al., "Studies on Neurokinin Antagonists. 3. Design and Structure–Activity Relationships of New Branched Tripeptides $N^{\alpha}$–(Substituted L–aspartyl, L–ornithyl, or L–lysyl)–N–methyl–N–(phenylmethyl)–L–phenylalaninamides as Substance P Antagonists," *J. Med. Chem.*, 36, 2266–2278 (1993).
Kodama, H, et al., "Dimerization of Neurokinin A and B COOH–Terminal Heptapeptide Fragments Enhanced the Selectivity for Tachykinin Receptor Subtypes," *Euro. J. Pharmacol.*, 151, 317–320 (1988).
Stewart, J. M., et al., "Chemistry of Peptide B2 Bradykinin Antagonists," In: *Bradykinin Antagonists—Basic and Clinical Research.*, Burch, R. M. (ed.), Marcel Dekker, Inc., pp. 51–96 (1991).
Stewart, J. M., et al., "Bradykinin Chemistry: Agonists and Antagonists," In: *Adv. Exp. Med. Biol.*, vol. 156, Fritz, H., (ed.), Plenum Press, New York, pp. 585–589 (1983).
Vavrek, R. J., et al., "Succinyl Bis–Bradykinins: Potent Agonists with Exceptional Resistance to Enzymatic Degradation," In: *Peptides—Structure and Function*, Hruby, V. J., et al., (eds.), Pierce Chemical Company, Rockford.

*Primary Examiner*—Christina Chan
*Assistant Examiner*—T. D. Wessendorf
*Attorney, Agent, or Firm*—John Burke

[57] ABSTRACT

The present invention provides a heterodimeric compound possessing bradykinin and neurokinin receptor antagonist activities useful in the treatment of asthma and other inflammatory diseases especially those involving the airway or pulmonary system. The present invention is also useful in the treatment of pain and inflammation.

10 Claims, No Drawings

BRADYKININ RECEPTOR ANTAGONISTS WITH NEUROKININ RECEPTOR BLOCKING ACTIVITY

This application is a continuation-in-part of U.S. Ser. No. 07/974,000 filed Nov. 10, 1992, abandoned, which is a continuation-in-part of U.S. Ser. No. 07/859,582 filed Mar. 27, 1992, abandoned, which is a continuation-in-part of U.S. Ser No. 07/677,391 filed Apr. 1, 1991, abandoned, the entire contents of each of the applications being incorporated herein by reference.

BACKGROUND OF THE INVENTION

This invention relates to compounds with combined bradykinin and neurokinin receptor antagonist activity and to methods of using the same.

Neurokinins (tachykinins) are a group of naturally occurring peptides found in a variety of human and mammalian tissues. Neurokinins are believed to be involved in a large number of physiological processes within the digestive, circulatory, pulmonary, central nervous and peripheral nervous systems. Substance P, a member of the neurokinin group, is believed to be involved in the neurotransmission of pain sensations [TIPS 8 506 (1987)] and has been implicated as playing an important role in pain or neurogenic inflammation in a number of disease states including migraine [D. Regoli in "Trends in Cluster Headache", Elsevier, p. 85, (1987) and B. Sandberg et al, *J. Med. Chem.* 25 1009 (1982)], arthritis [Gronblad et al, *J. Rheumatol.* 15 1807 (1988)], and inflammatory bowel disease [Mantyh et al, *Neuroscience* 25 817 (1988)].

Substance P is stored in primary sensory C-fibers, while in the airway, it is found in nonmyelinated afferent C-fibers. Stimulation of these nerve fibers by the action of bradykinin, antigens, capsaicin, chemical or mechanical irritation, can cause the release of substance P [C. R. Martling et al, *Life Sciences* 40 1633 (1987)] stimulating a number of airway inflammatory responses including edema formation, mucus secretion, inflammatory cell infiltration and cough. [J. A. Lowe in Annual reports in Medicinal Chemistry 28 99 (1993)]. Substance P has been implicated in the pathophysiology of several airway disorders including bronchitis and asthma.

The $NK_1$ receptor (the neurokinin receptor with the highest specificity for substance P) has extensive pulmonary distribution and is found on both epithelial cells and endothelial cells, as well as on several types of circulating leukocytes. $NK_1$ receptor antagonist capable of blocking this receptor would have broad application in treating or eliminating a large number of disease states such as those described above. In addition, neurokinin receptor antagonists may be useful in treating demyelinating disorders such as multiple sclerosis and amyotrophic lateral sclerosis.

A large number of both peptide and nonpeptide neurokinin type 1 ($NK_1$) receptor antagonists are known. Recently, it has been demonstrated that several non-peptide $NK_1^a$ antagonists exhibit nonspecific action and interact with calcium channels or exhibit unusual non-competitive antagonist action on $NK_1$ receptors in isolated tissues. Fujisawa has reported two peptide based antagonists, FR113680 and FK888. Although both of these compounds are specific $NK_1$ antagonists, FR113680 lacks sufficient potency, stability, and solubility to be a viable pharmaceutical agent [Hagiwara, D. et al, *J. Med Chem.* 35:3184 (1992)]. FK888, although more potent than FR113680, does not approach the potency of Pfizer CP-99994 (Desai, M. C. et al, *J. Med. Chem.* 35:4911–4913 (1993)), which is reported to be 10 times more potent than FK888 in binding studies. In addition, FK888 also has poor water solubility characteristics, a factor that limits its application as an inhaled, injected or intravenously administered drug.

FR113680 is a species generically represented by the formula: $R^1$-A-D-Trp-Phe($NR^2$)-$R^3$, where $R^1$ is hydrogen or an amino protective group; A is one or two amino acid residues, and $R^2$ is lower alkyl and $R^3$ is alkylaromatic. Although a number of suitable protective groups for $R^1$ have been defined, succinimido-alkanylcarboxylates, or peptides attached to such structures have not been described. (See, for example, European Patent Application (EPA) 89104617.9)

Patent applications related to EPA 89104617.9, such as EP patent application 90107822.0, U.S. Pat. No. 5,164,372, and WO 92JP780 describe structures of the general formula:

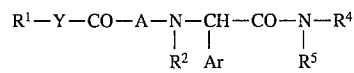

wherein A is an amino acid with "suitable substituents." Although lysine is mentioned in these documents succinimido-alkanylcarboxylates, or peptides attached through such structures are not described as suitable substituents for A. In publications related to the disclosure of FK-888 (such as EP 90123875) A in the above general formula is defined specifically as proline or a closely related structure. Publications dealing with these classes of compounds specifically dissuade one skilled in the art from making substitutions or additions at A. For example, FR113680 was shown to have a binding constant of $5.8 \times 10^{-9}$ Molar on isolated guinea pig lung membrane [Hagiwara et al, *J. Med Chem.* 35 3148 (1992)], while analogs incorporating Lys at position A, were all at least 10 fold less potent than this parent compound, and substituents on this Lys residue at the α-amino nitrogen produced compounds of lesser or equal potency than FR113680. [Hagiwara et al, *J. Med. Chem* 36 2266 (1993)]. Compounds such as compound CP-0533, described herein, which was reported by Fujisawa, showed, in the absence of organic solvents, minimal water solubility and gave poor assay results.

Bradykinin (BK) is an endogenous peptide hormone released by proteolytic cleavage of kininogen by a group of endopeptidases known as kallikreins. Bradykinins are mediators in eliciting many pathophysiological responses including pain and hyperalgesia via stimulation of peripheral A- and C-fiber neurons [Farmer, S. G. in *Bradykinin Antagonists*, R. M. Burch, ed., Marcel Dekker, Inc. New York, pp. 1–31, (1991); Griesbacher, T., *Br. J. Pharmacol.*, 92:333–340 (1987); Taiwo, Y. O., *Brain Res.*, 458:402–406 (1988); Steranka, I. R. et al, *Proc. Nat. Acad. Sci.* USA, 85:3245–3249 (1988); Dray, A., *Neurosci. Lett.*, 91:301–307 (1988); Sterankan, L. R., *FASEB J.*, 3:2019–2025 (1989); *Neurosci. Lett.*, 97:198–202 (1989)].

In addition, there is evidence that BK plays an important role in inflammatory response [Marceau, F., *Gen. Pharmacol.*, 14:209–229 (1983); Proud, D., *Annu. Rev. Immunol.*, 6:49–84 (1988); Colman, R. W. in Bradykinin, Kallidin and Kallikrein, *Handbook of Experimental Pharmacology*, Vol. 25, Erdos, E. G. ed., Springer Verlag, New York (1979); Greaves, M. W., *Br. J. Dermatol.*, 119:419–426 (1988)] and is a significant mediator in several disease states including hypotension associated with sepsis, [Thrombosis and Haemostasis, 58:709–719 (1978); Whalley, E. T., Agents and Actions, 38:413–420 (1992)] and bronchopulmonary disorders including asthma [Farmer, S. G. in *Bradykinin Antago*- nists, R. M. Burch, ed., Marcel Dekker, Inc., New York, pp. 213–236 and 261–276 (1991)]. There is also compelling evidence that bradykinin receptor antagonists may be useful in the treatment of edema (swelling) in head trauma, [Unterberg, A., *J. Neurosurgery,* 64:269–276 (1986)] edema and pain from severe burns, [Holder, I. A., *Journal of Burn Care and Rehabilitation,* 11:496503 (1990).], migraine pain, [Sicuteri, F., *Res. Clin. Stud. Headache,* 1:6 (1967)] and pain associated with surgical procedures or cancer. Recent animal studies also indicate that bradykinin receptor antagonists may be extremely efficacious in prolonging survival in cases of severe general trauma [Christopher, T. A. et al., *Am. J. Physiol.* 226:H867-H873 (1994)]. Notwithstanding prior efforts, there remains a considerable need to provide improved BK and $NK_1$ antagonists with useful receptor antagonist and pharmaco-kinetic properties. The main object of the present invention is to provide such receptor antagonists which include $BK-NK_1$ antagonist heterodimers demonstrating superior synergistic action, improved activity and increased solubility under physiological conditions.

SUMMARY OF THE INVENTION

The invention is based on the concept of providing compounds with combined $NK_1$ and BK receptor antagonist components for treating pain and neurogenic inflammation. The receptor antagonists of the present invention are considered to be particularly useful in the treatment or management of inflammatory diseases, such as asthma, where bradykinin and substance P are suspected of generating a number of the overt symptoms and exacerbating the underlying chronic inflammatory response. Under such conditions, compounds exhibiting combined $NK_1$ receptor and bradykinin receptor antagonist activity should be extremely advantageous.

Previously, the inventors have shown that heterodimeric bradykinin receptor antagonist constructs having diverse activity may be made by incorporating non-peptide bisuccinimidoalkanoyl linked ligands. Such compounds are described in the commonly owned and co-pending U.S. patent application Ser. No. 07/974,000continuation parent of application Ser. No. 08/440,338, the entire contents of which are incorporated herein by reference. The present invention diverges from the use of the bis-succinimido linkages for heterodimer formation, resulting in constructs which are easier to synthesize, purify and characterize chemically, due to the reduction in stereocenters associated with the creation of cross-link between the BK antagonist and the peptoid ligand. It has also been demonstrated by the inventors that alternative linking moieties are capable of increasing BK receptor antagonist potency as is described in copending U.S. patent application Ser. No. 08/077,998, the entire contents of which is incorporated herein by reference.

The present invention relates to compounds with combined bradykinin and neurokinin receptor antagonist activity. More specifically, the compounds of the invention can be described as heterodimeric constructs composed of two peptide or peptide-like chains covalently attached by a succinimide or related linkage. The combined heterodimeric structures have a number of beneficial properties not found in the isolated monomeric peptides. Thus, these compounds demonstrate properties useful in the treatment of asthma and other inflammatory diseases, especially those involving the airway or pulmonary system, and in the treatment of pain and inflammation, especially pain and inflammation related to surgical procedures or migraine.

DETAILED DESCRIPTION OF THE INVENTION

The present invention provides heterodimeric compounds of the formula:

BKA-X wherein BKA is a bradykinin receptor antagonist and X is a neurokinin receptor antagonist. More specifically, the present invention provides compounds of the formula (A), or a salt or pro-drug thereof:

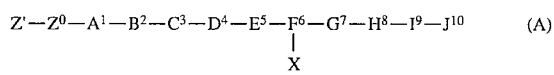

wherein:

Z' is optionally absent, but if present, is hydrogen, acetyl, adamantylcarboxyl, adamantylacetyl, (C1 to C8 straight chain or branched)-alkyl, -alkanoyl, arylsufonyl or alkoxycarbonyl or a derivative of a dihydroquinuclidinyl-carboxylic acid;

$Z^0$ is optionally absent but, if present, is D or L arginine, D or L lysine, D or L ornithine, $H_2N(NH=C)NHCH_2CH_2CH_2(CH_2)_nCO-$, (where n is an integer from 0 to 3) or arginine substitutes;

$A^1$ is D or L arginine, D or L lysine, D or L ornithine or arginine substitutes;

$B^2$ is proline, hydroxyproline, glycine, serine, threonine, N-methyl serine, N-methyl threonine or NR'CHR"CO wherein R' and R" are independently hydrogen, alkyl (e.g., C1–C8 straight chain, or branched or C3–C8 cycloalkyl), monocyclic or polycyclic aryl, heteroaryl or alkyl amino;

$C^3$ is proline, hydroxyproline, glycine, serine, threonine, N-methyl serine, N-methyl threonine or NR'CHR"CO wherein R' and R" are independently hydrogen, alkyl (e.g., C1–C8, straight chain or branched or C3–C8 cycloallkyl), monocyclic or polycyclic aryl, heteroaryl, or alkyl amino;

$D^4$ is glycine, alanine, or thienylalanine;

$E^5$ is phenylalanine, phenylalanine substituted with methyl groups, glycine, cyclopentylglycine, cyclohexylglycine, cyclohexylalanine, 2-indaneglycine, 2-thienylalanine, N-(2-indane) -glycine, or N-substituted glycine, where the substituent is alkyl (e.g., C1–C8 straight chain or branched), C3–C8 cycloalkyl, monocyclic or polycyclic aryl or substituted aryl wherein said substituent is C1–C2 alkyl, alkylthienyl, or an aromatic amino acid, or an aromatic amino acid substituted at the α-nitrogen or α-carbon with a methyl or ethyl group;

$F^6$ is cysteine, homocysteine, peniciliamine, β-methylcysteine, or an amino acid residue containing a thiol moiety;

$G^7$ is an aromatic amino acid, such as, D-Tic, D-phenylalanine, 2-indaneglycine, D-cyclopentylglycine, D-cyclohexylglycine, D-proline or proline substituted at the 3 or 4 position with C1–C8 straight chain or branched alkyl, monocyclic or polycyclic aryl, thioalkyl, thioaryl, oxyalkyl, or oxyaryl substituents;

$H^8$ is an amino acid, such as phenylalanine, leucine, Oic, norvaline, cylopentylglycine, cyclohexylglycine, or glycine residues substituted at nitrogen with C1–C8 straight chain or branched alkyl, cycloalkyl, or monocyclic or polycyclic aryl substituents;

$I^9$ is OH, or a basic, acidic, or neutral amino acid, preferably, arginine, lysine, $H_2N(NH=C)NHCH_2CH_2CH_2(CH_2)_n-NH-$, (where n is an integer from 0 to 3) or arginine substitutes;

$J^{10}$ is optionally absent, but, if present, is OH; and

X is as shown in Formula I or Formula II.

Formula I is:

$$\text{[structure: indole with } R^2 \text{ on N, attached to } R^1-A-N(H)-C(H)(\cdots)-C(O)-L-N(R^3)(R^4)\text{]}$$

wherein $R^1$ is defined as: —Z—$(CH_2)_m$—CO— where Z is a succinimido, phenyl or pyrrolidinone group and the sulfur atom of $F^6$ is attached to Z via a covalent bond; the attachment may be direct or mediated by one methylene ($CH_2$) unit, and m is an integer from 1 to 8;

A is defined as an amino acid residue;

L is defined as phenylalanine, tyrosine, 3-(2-napthyl)-alanine, 2-indaneglycine or Tic or (N-methyl)-phenylalanine, (N-methyl)-tyrosine, (N-methyl)-3-(2-napthyl)-alanine, or (N-methyl)-2-indaneglycine;

$R^2$, the indole nitrogen substituent, may be H, methyl, formyl, acetyl, lower alkyl, or substituted carboxyl containing lower alkoxy or lower alkyl substituents, wherein lower alkyl or lower alkoxy is defined as containing 1–8 carbon atoms;

$R^3$ is defined as methyl or lower alkyl; and $R^4$ is defined as benzyl, substituted benzyl, phenethyl, lower alkyl, isopropyl, isobutyl, sec-butyl, isoamyl or —$CH_2CH_2$—$R^5$, where $R^5$ is indole.

Formula II is defined as:

$$R^6-CO-P-L-N(R^3)(R^4)$$

where $R^6$ is defined as $$\text{[structure: benzene ring with substituents =R and Q]}$$

where R is nitrogen or CH, and Q is NH, or N—$R^1$;

and

P is defined as:

$$-NH-C(-(CH_2)_m-Z)-CO-$$

here m=1 to 8, and Z is a succinimido, phenyl or pyrrolidinone group or a substituted succinimido, phenyl or pyrolidinone group where the sulfur atom of $F^6$ is attached to Z via a covalent bond, the attachment being direct or mediated by one methylene ($CH_2$) group and the substitution is C1–C8 straight chain or branched alkylamide; and L is phenylalanine, tyrosine, 3-(2-napthyl)-alanine, 2-indaneglycine or Tic.

As used herein, the term "arginine substitutes" refers to common replacements for arginine as practiced in the art of medicinal chemistry which produce a positively charged heteroatom at physiological pH. These include, but are not limited to, analogs and homologs of arginine, ornithine, or lysine containing alkylamines, benzamidine, piperidines, alkylguanidines or alkylphosphonium moieties.

As used herein, the term "aryl" or "Ar" includes phenyl, naphthyl, biphenyl, indane or fluorene.

As used herein, the term "heteroaryl" refers to monocyclic or polycyclic aromatic ring systems containing five to fourteen atoms, including carbon and at least one atom selected from nitrogen, oxygen or sulfur. These include, but are not limited to, pyrrole, pyridine, indole, oxazole, pyrazole, pyrimidine, purine, guanine, adenine, pyrazine, quinoline, isoquinoline, furan, benzofuran, benzoxazole, thiophene, benzothiophene and thiazole.

In general, the three-letter codes commonly accepted for amino acids have been used (European *J. Biochemistry* 138 9 (1984)). Additional abbreviations are as listed below:

| Boc | tert-Butyloxycarbonyl |
|---|---|
| BOP | Benzotriazol-1-yloxy-tris(dimethylamino)phosphonium hexafluorophosphate |
| Bop-Cl | bis(2-oxo-3-oxazolidinyl)phosphinic chloride |
| CP-0126 | D-Argininyl-L-argininyl-L-prolyl-(4R-hydroxy)-L-prolyl-glycyl-L-phenylalanyl-L-cysteinyl-D-phenylalanyl-leucyl-arginine |
| Cpg | cyclopentylglycine |
| DMF | dimethylformamide |
| LD-MS | Laser-Desorption Mass Spectrum |
| Oic | cis-endo-octahydroindol-2-carbonyl |
| PyBrop | bromo-tris-pyrrolidino-phosphonium hexafluorophosphate |
| TFA | trifluroacetic acid |
| Tic | 1,2,3,4-tetrahydroisoquinolin-3-yl-carbonyl |
| Thi | 2-thienylalanine |
| Nal | 3-(2-napthyl)-alanine |

The invention is based on the discovery that linking of a peptoid neurokinin ($NK_1$) receptor antagonists to bradykinin receptor antagonists via a succinimido or other suitable linkage, provides compounds with combined antagonist activity at BK and $NK_1$ receptors. In a subsidiary feature, it has also been found that the introduction of the monomeric peptides or peptoids into a heterodimer construct of the present invention provides at least one of:

increased $NK_1$ receptor antagonist potency;

increased $BK_2$ receptor antagonist potency;

decreased reversibility of antagonist/receptor interaction as measured by "wash-off" or recovery experiments;

increased stability of bradykinin peptide construct to enzymatic degradation;

increased water solubility of neurokinin peptoid which facilitates their use as injectable, inhalable or intravenously administered drugs; and possible sequestering of the activity of the neurokinin peptoid from the central nervous system, believed to be due to the covalent attachment of highly positively charged BK receptor antagonist.

Increased receptor antagonist potency and decreased reversibility of receptor/antagonist interaction is demonstrated by any of the following representative compounds of the instant invention.

Compound 1, a representative compound of the present invention, where X is Formula I, was found to have a larger apparent $NK_1$ p$A_2$ value (7.3) as compared with FR113680 reported by Fujisawa, and the antagonism produced by the inhibitor is essentially irreversible (0% recovery) as measured by in vitro wash-off experiments. One skilled in the art will appreciate that chemical structures used in this disclosure are for illustrative purposes only—the actual and/or relative bond lengths may not be accurately reflected.

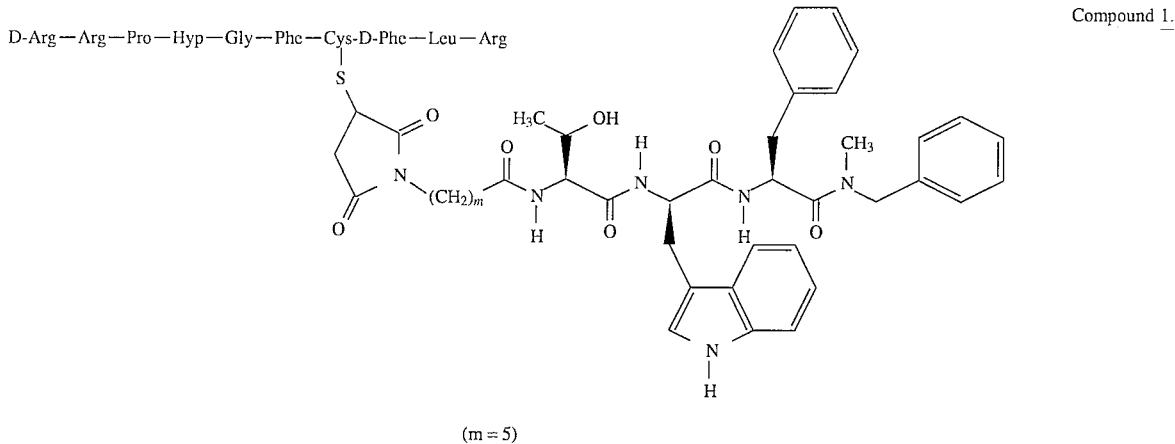

Compound 1.

(m = 5)

The apparent $BK_2$ $pA_2$ value (8.0) for Compound 1, represents approximately an order of magnitude increase in potency in the rat uterus functional tissue assay when compared to the bradykinin receptor antagonist portion of Compound 1 alone, and the recovery of activity in wash off experiments for the $BK_2$ receptor decreases from 100% to 20% when compared to the uncoupled bradykinin receptor antagonist above. Addition of a succinimide group and linker functionality alone to X, when X is Formula I, such as the following control compound CP-0528, does not confer enhanced properties to the $NK_1$ receptor antagonist. With CP-0528, $NK_1$ receptor antagonist activity is only slightly attenuated ($pA_2$ =6.5) by the addition of the succinimide linker functionality.

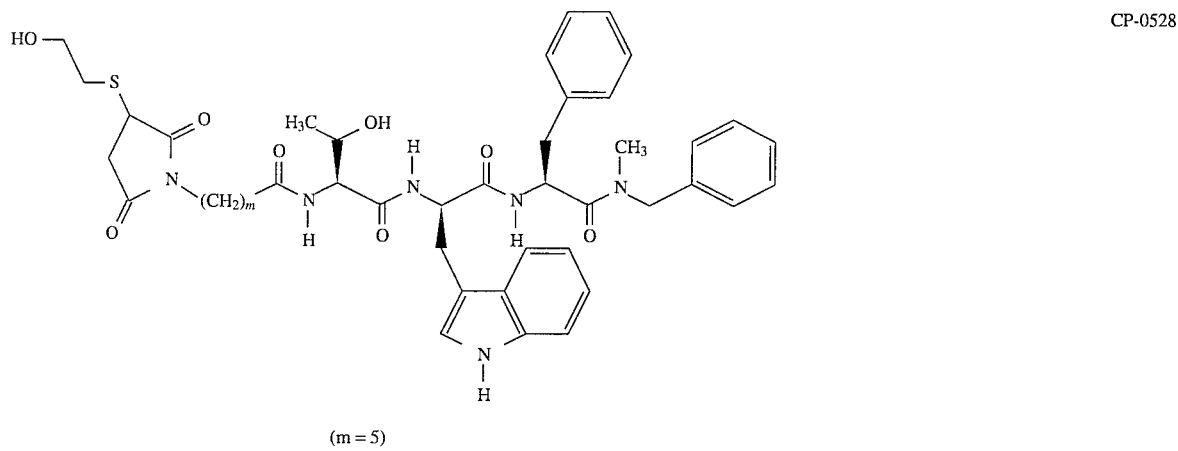

CP-0528

(m = 5)

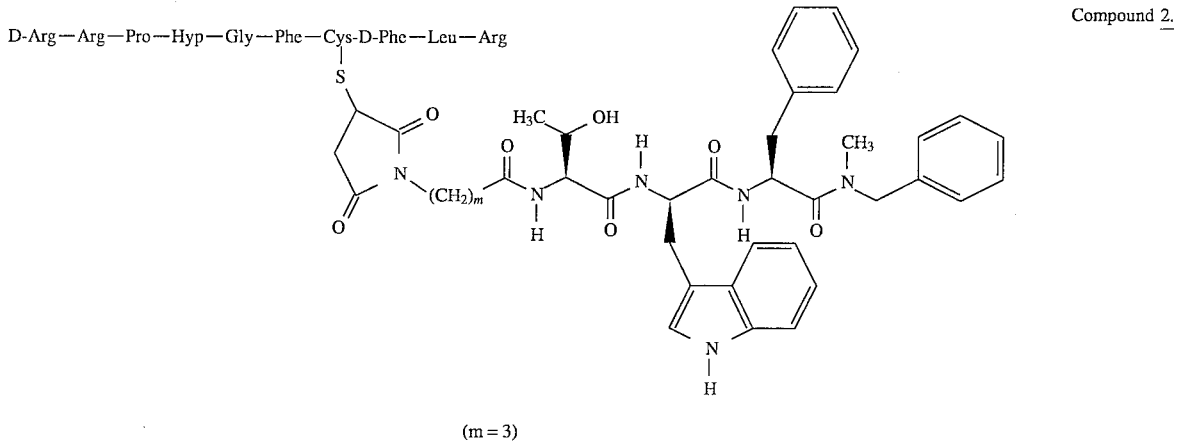

Compound 2.

(m = 3)

Compound 2, wherein the linker appendage has been shortened as compared to Compound 1, produces a compound with more than an order of magnitude increase in $BK_2$ receptor antagonist potency ($pA_2$= 8.2) when compared to the bradykinin receptor antagonist alone.

As with the comparison of Compound 1 and CP-0528, addition of the succinimide group and linker functionality alone to the $NK_1$ receptor antagonist portion of the heterodimer does not confer enhanced properties to the $NK_1$ receptor antagonist. This is evidenced by the control analog CP-0529 in which NK$_1$ receptor antagonist activity (pA$_2$=6.9) is not affected by the addition of the succinimide linker functionality.

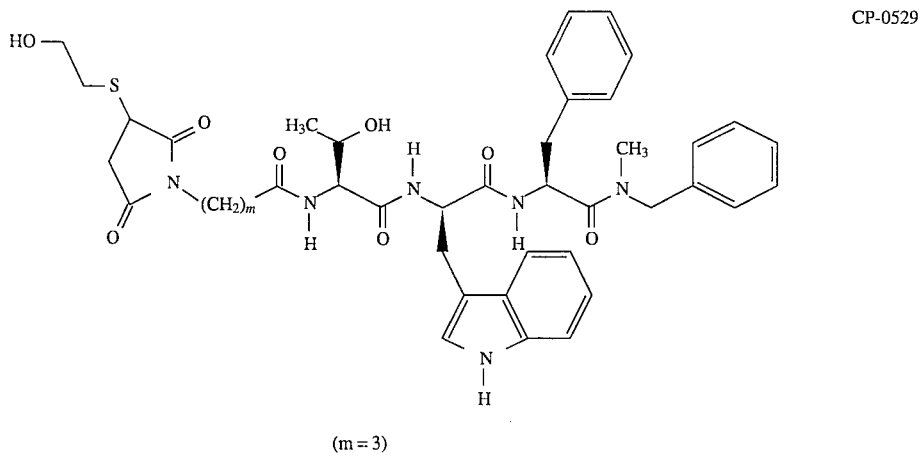

CP-0529

(m = 3)

CP-0533 has been found to be a modestly potent NK$_1$ receptor antagonist (pA$_2$=6.3, 73% recovery). Despite the fact that CP-0533 was tested as a hydrochloride salt, it exhibited poor solubility in water and required the addition of organic co-solvents for the purpose of the biological assays.

Compound CP-0533 exemplifies NK$_1$ receptor antagonists according to the present invention where X in formula (A) is structurally similar to formula II, where L is phenylalanine and Z is replaced by an amino substituent.

enhanced, as evidenced by low recovery (29% versus 100%) in wash-off experiments. CP-0126 is D-Arg-Arg-Pro-Hyp-Gly-Phe-Cys-D-Phe-Leu-Arg. NK$_1$ receptor antagonist potency was significantly increased (pA2=6.9, 53% recovery), however, relative to CP-0533. Accordingly, solubility, and hence utility of the presently disclosed class of NK$_1$ receptor antagonists is increased when combined in the instantly disclosed heterodimers, while the BK receptor antagonist activity of the disclosed heterodimer is enhanced in its binding affinity for BK receptor, as measured in wash-off studies.

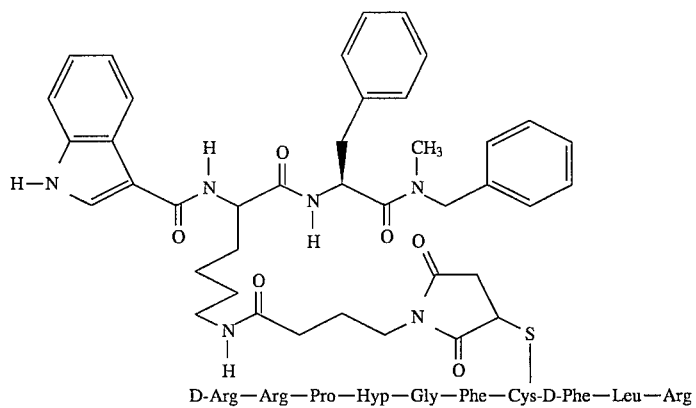

Compound 3.

D-Arg—Arg—Pro—Hyp—Gly—Phe—Cys-D-Phe—Leu—Arg

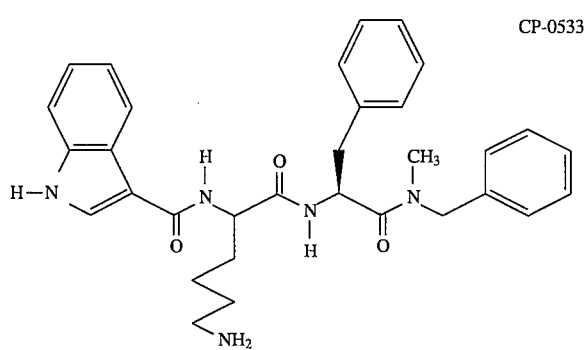

CP-0533

In Compound 3, BK$_2$ receptor antagonist potency was not significantly increased, relative to CP-0126, a potent BK$_2$ receptor antagonist described by Cheronis et al (*J. Med. Chem.* 35:1563 (1992)), although the irreversibility was Compound 4 of the present invention represents a preferred embodiment of the invention wherein X in formula (A) is formula II, and, in this example, L is 3-(2-naphthyl)-alanine.

The parent NK$_1$ receptor antagonist ligand, CP-0535, has been found to be a moderately potent NK$_1$ receptor antagonist (pA$_2$=7.5) that exhibited poor water solubility when tested as the hydrochloride salt. As with CP-0533, the addition of organic solvents was necessary to obtain sufficient concentrations for biological assays. Addition of a succinimido linker, as in the case of control analog CP-0580, has been found to produce an increase in NK$_1$ receptor antagonist potency (pA$_2$=8.0) relative to CP-0535. Without wishing to be bound to any theoretical explanation, this relatively large effect is postulated to be due to the reduction of charge presented by the ε-ammonium group of the lysine in CP-0535. Formation of a heterodimer between CP-0535 and CP-0126 via a succinimido linkage produces a compound (Compound 4) with exceptional NK$_1$ receptor antagonist activity (pA$_2$=9.0) and low (12%) recovery in wash-off experiments.

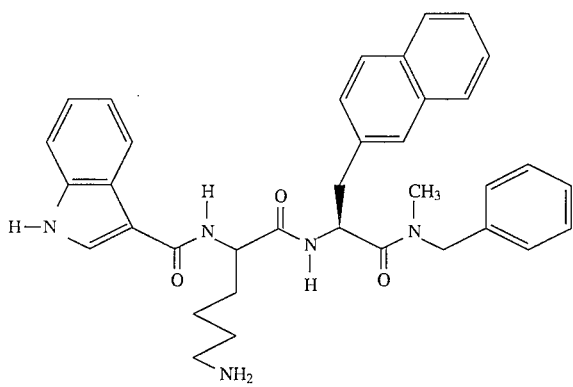

CP-0535

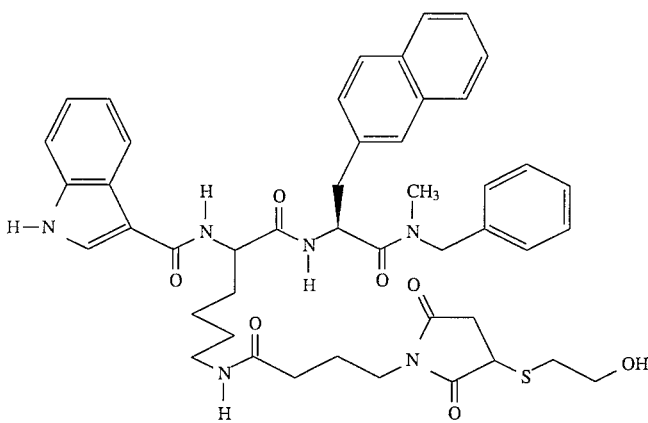

CP-0580

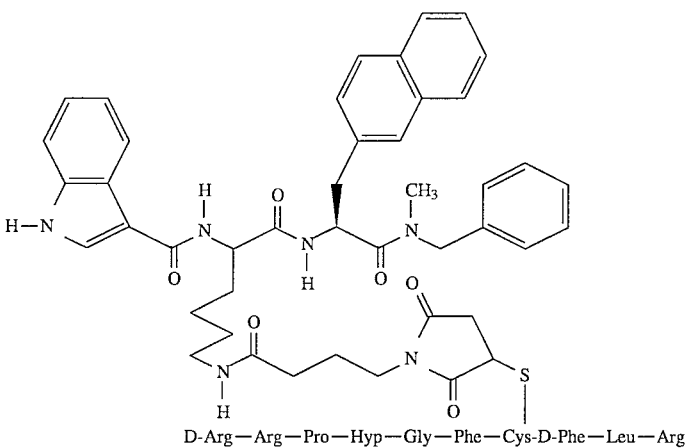

Compound 4

D-Arg—Arg—Pro—Hyp—Gly—Phe—Cys-D-Phe—Leu—Arg

The most preferred compounds of the present invention are antagonists of bradykinin and neurokinins receptors which have wide utility for therapeutic intervention in disease states or pathophysiologic conditions where the action of bradykinin and neurokinins are implicated. Protocols are described in the following examples for determining bradykinin and neurokinin receptor antagonist activity using in. vitro and in vivo assays which verify the potential usefulness of particular compounds for the treatment of inflammatory response, in particular, inflammation of the airway or pulmonary system. In addition, in vitro assays for gauging the potential stability of compounds in vivo are described. The heterodimeric constructs of the present invention, as represented by Compounds 1–4, are fully water soluble at concentrations required for in vitro and in vivo assays.

Neurokinin 1 (NK$_1$) receptor antagonist effects were measured by pA$_2$ values determined on isolated guinea pig ileum segments using Substance P-O-methyl ester as a contraction stimulating agonist. Bradykinin 2 (BK$_2$) receptor antagonist effects were measured by pA$_2$ values determined on isolated rat uterus segments using bradykinin as a contraction stimulating agonist. The control analogs used were CP-0126 (D-Arg-Arg-Pro-Hyp-Gly-Phe-Cys-D-Phe-Leu-Arg), a previously reported bradykinin antagonist [Cheronis et al, *J. Med. Chem.* 5:1563 (1992)] (BK$_2$ pA$_2$= 7.1, 100% recovery), and FR113680 [Ac-Thr-D-Trp-Phe-N(CH3)Bn], a moderately potent neurokinin antagonist (NK$_1$ pA2=7.0, 53% recovery) with poor water solubility and moderate in vivo stability [Hagiwara, D. et al, *J. Med. Chem.* 35:3148 (1992)].

Therapeutic application of compounds described herein with combined bradykinin and neurokinin receptor antagonists activity include traumatic, inflammatory or pathological conditions mediated by bradykinins and neurokinins or their closely related metabolites. These conditions may include treatment of bites, stings, general trauma, head trauma, inflammatory conditions including inflammatory bowel disease, burns, rashes, shock or hypotension associated with sepsis and pain, especially pain associated with surgical or dental procedures, or migraine pain. In addition, the presently disclosed antagonists may be used for the treatment of airway hypersensitivity and inflammation, as well as other symptoms associated with asthma.

The compounds of the present invention may be administered topically, or by injection or infusion or as an oral suspension in an appropriate vehicle or as tablets, pills, capsules, caplets or the like. The dosage and manner of administration will be defined by the application of the bradykinin/neurokinin antagonist and can be determined by routine methods of clinical testing to determine the optimum dose. These doses are expected to be in the range of 0.001 mg/Kg to 100 mg/Kg of active compound. The compounds are composed of amino acids which may form salts due to their acidic or basic nature, and any pharmacologically acceptable salt derived from the instantly disclosed compounds, such as hydrochlorides, acetates, phosphates, maleates, citrates, benzoates, salicylates, succinates, ascorbates and the like, are considered to be within the scope of the present invention. One skilled in the art will appreciate that a common tactic in medicinal chemistry is to modify known drug substances which are peptide based to form esters or amides which exhibit greater bioavailability. Prodrugs derived from the compounds disclosed herein are therefore considered part of this invention.

The invention is described further by the following examples. These examples are intended to be illustrative and instructive and are not intended to be limiting.

EXAMPLES

EXAMPLE I—Synthesis of Compound 1

A. 6-(1-Maleimido)-Hexanoyl-L-Threonyl-$N^{Im}$-Formyl-D-Trypto-phanyl-L Phenylalanine N-(Methyl)Benzylamide: L-Threonyl-$N^{Im}$-formyl-D-tryptophanyl-L-phenylalanine N-(methyl)-benzylamide (219 mg, 0.377 mmole, synthesis is described below), 6-(1-maleimido)-hexanoic acid (79 mg, 0.38 mmole), and N,N-diisopropylethylamine (0.166 mg, 0.377 mmole) were dissolved in dichloromethane (10 mL). BOP reagent (166 mg, 0.377 mmole) was added and the reaction stirred under nitrogen at room temperature for approximately 15 hours. The reaction mixture was then diluted with dichloromethane and worked up according to general method A. The resulting foam was purified by chromatography on silica gel eluting with 2–6% MeOH in $CH_2Cl_2$, to yield 197 mg of the title compound as a colorless foam.

Compound 1: 6-(1-Maleimido)-hexanoyl-L-threonyl-$N^{Im}$-formyl-D-tryptophanyl-L-phenylalanine N-(methyl)-benzylamide (19 mg) was treated with 1 mL of dimethylformamide to which was added approximately 100 mL of a 100 mMolar solution of ammonium bicarbonate in water. CP-0126 [Cheronis et al, *J. Med. Chem.* 35:1563 (1992)] (tetra trifluroacetate salt, 42 mg) was added. The reaction was then stirred 2 hours at room temperature under nitrogen. The mixture was purified by preparative C-18 HPLC (25× 300 mm column) using a gradient of 5–85% $CH_3CN$ (0.1% TFA) over 60 minutes. Flow rate was 10 mL/min. Lyophilization of appropriate fractions provided 36 mg of the title compound as a colorless lyophilate. C18-HPLC 25–85% $CH_3CN$ (0.1% TFA), over 40 minutes. Retention time 16.3 minutes. LD-MS Calculated 2042 Found 2042. AAA Gly 1.09 (1), Arg 2.97 (3) Thr (1.14) Pro 1.02 (1) , Cys (observed, not quantitated), Phe 2.87 (3) Hyp 0.96 (1).

EXAMPLE II—Synthesis of Compound 2

A. tert-Butyloxycarbonyl-L-Phenylalanine N-(Methyl)Benzylamide: tert-Butyloxycarbonyl-L-phenylalanine (5.99 g, 22.6 mmole), N-(methyl)-benzylamine (2.78 mL, 21.5 mmole), diisopropylethylamine (9.4 mL, 53.8 mmole) were dissolved in 75 mL of dichloromethane and chilled to 0 C under nitrogen. Bis(2-oxo-3-oxazolidinyl)phosphinic chloride (6.57 g, 25.8 mmole) was added and the reaction stirred at 0 to 5 C for approximately 15 hours. The reaction mixture was diluted with dichloromethane and worked up according to method A. The resulting foam was purified by chromatography on silica gel eluting with 50% acetone in hexanes. Pooling of appropriate fractions, removal of solvent and drying under high vacuum provided the title compound (6.0 g) as a colorless oil.

B. L-Phenylalanine N-(Methyl)Benzylamide: tert-Butyloxy carbonyl-L-phenylalanine N-(methyl)benzylamide (5.23 g) was deblocked according to general method B, to yield the title compound (3.43 g) as an oil.

C. $N^{\alpha}$-tert-Butyloxycarbonyl-$N^{Im}$-Formyl-D-Tryptophanyl-L-Phenyl- alanine N-(Methyl)Benzylamide: $N^{\alpha}$-tert-butyloxycarbonyl-$N^{Im}$-formyl-D-tryptophan (951 mg, 2.86 mmole) was dissolved in 20 mL dimethylformamide, chilled to 0 C under nitrogen and 1-hydroxybenzotriazol-hydrate (927 mg, ~6.86 mmole) and 1-(3-diaminopropyl)-3-ethylcarbodiimide hydrochloride (576 mg, 3.00 mmole) were added. The reaction mixture was allowed to stir for one hour then L-phenylalanine N-(Methyl)benzylamide (840 mg, 3.14 mmole) was added. The reaction mixture was allowed to warm to room temperature and stirring was continued for 48 hours. Work-up according to genera 1 method A, provided the title compound (1.07 g) as a foam.

D. $N^{Im}$-Formyl -D-Tryptophanyl-L-Phenylalanine N-(Methyl)-Benzyl- amide: $N^{\alpha}$-tert-butyloxycarbonyl-$N^{Im}$-formyl-d-tryptophanyl-1-phenylalanine N-(methyl)-benzylamide was deprotected according to general method B.

E. $N^{\alpha}$-tert-Butyloxycarbonyl-L-Threonyl-$N^{I}$-Formyl-D-Tryptophanyl-L-Phenylalanine N-(Methyl)-Benzylamide: $N^{\alpha}$-tert-Butyloxycarbonyl-L-threonine (284 mg, 1.29 mmole) was coupled to $N^{Im}$-formyl-D-tryptophanyl-L-phenylalanine N-(methyl)-benzylamide (567 mg, 1.18 mmole) using general method C. After four hours, the reaction was worked-up according to general method A. Removal of the solvent and drying under high vacuum provided the title compound (774 mg) as a colorless foam.

F. L-Threonyl-$N^{Im}$-Formyl-D-Tryptophanyl-L-Phenylalanine N-(Methyl)-Benzylamide: $N^{\alpha}$-tert-Butyloxycarbonyl-L-threonyl-$N^{Im}$-formyl-D-tryptophanyl-L-phenylalanine N-(methyl)-benzylamide (774 mg) was deprotected according to general method B, to provide the title compound that was isolated as a colorless foam.

G. 4-(1-Maleimido)-Butanoyl-L-Threonyl-$N^{Im}$-Formyl-D-Trypto-phanyl-L-Phenylalanine N-(Methyl)Benzylamide: L-Threonyl-$N^{Im}$-formyl-D-tryptophanyl-L-phenylalanine N-(methyl)-benzylamide (274 mg, 0,470 mmole), 4-(1-maleimido)-butanoic acid (86 mg, 0.47 mmole), N,N-diisopropylethylamine (0.262 mL, 1.50 mmole) were dissolved in dichloromethane (10 mL). BOP reagent (208 mg, 0.470 mmole) was added and the reaction stirred under nitrogen at room temperature for 3.5 hours. The reaction mixture was then diluted with dichloromethane and worked up according to general method A. The resulting foam was purified by chromatography on silica gel eluting with 2–6% MeOH in $CH_2Cl_2$ to yield 258 mg of the title compound as a colorless foam.

Compound 2: 4-(1-Maleimido)-butanoyl-L-threonyl-$N^{Im}$-formyl-D-tryptophanyl-L-phenylalanine N-(methyl)-benzylamide (13 mg, 17 mmole) was treated with 1 mL of dimethylformamide to which was added approximately 100 mL of a 100 mMolar solution of ammonium bicarbonate in water. CP-0126 [Cheronis et al, J. Med. Chem 35 1563 (1992)] (tetra trifluroacetate salt, 30 mg, ~17 mmole) was added. The reaction was then stirred 4 hours at room temperature under nitrogen. The mixture was purified by preparative C-18 HPLC (25×300 mm column) using a gradient of 25–85% $CH_3CN$ (0.1% TFA) over forty minutes. Flow rate of 10 mL/min. Lyophilization of appropriate fractions provided 23 mg of the title compound as a colorless lyophilate. C18-HPLC 25–85% $CH_3CN$ (0.1% TFA), over 40 minutes. Retention time 20.9 minutes. LD-MS Calculated 2012 Found 2012.

EXAMPLE III—Synthesis of Compound 3

A. $N^\alpha$-tert-Butyloxycarbonyl-$N^\epsilon$-Benzyloxycarbonyl-L-Lysyl-L-Phenylalanine N(Methyl)Benzylamide: $N^\alpha$-tert-Butyloxycarbonyl-$N^\epsilon$-benzyloxycarbonyl-L-Lysine (672 mg, 1.77 mmole) was coupled to L-phenylalanine N-(methyl)benzylamide (450 mg, 1.68 mmole) by general method C. Extractive work up according to general method A, provided the title compound (921 mg) as a colorless oil of sufficient purity for synthetic purposes.

B. $N^\epsilon$-Benzyloxycarbonyl-L-Lysyl-L-Phenylalanine N-(Methyl) Benzylamide: $N^\alpha$-tert-Butyloxycarbonyl-$N^\epsilon$-benzyloxycarbonyl-L-lysyl-L-phenylalanine N-(methyl)benzylamide (921 mg) was deblocked by general method B to yield the title compound (654 mg) as a colorless oil.

C. $N^\alpha$-3-Indolecarbonyl-$N^\epsilon$-Benzyloxycarbonyl-L-Lysyl-L-Phenyl- alanine N(Methyl)Benzylamide: 3-Indolecarboxylic acid (144 mg, 0.90 mmole), $N^\epsilon$-benzyloxycarbonyl-L-lysyl-L-phenylalanine N-(methyl)- benzylamide (474 mg, 0.90 mmole), and diisopropylethylamine (0.50 mL, 2.9 mmole) were dissolved in 10 mL of dichloromethane, and treated with BOP (396 mg, 0.90 mmole). After four hours the reaction was worked up according to general method A. Silica gel chromatography eluting with 45% acetone in hexanes, provided 262 mg of the title compound as a colorless foam.

D. (CP-0533 Hydrochloride Salt): $N^\alpha$-3-Indolecarbonyl-$N^\epsilon$-Benzyl- oxycarbonyl-L-Lysyl-L-Phenylalanine N-(Methyl)Benzylamide (250 mg) was dissolved in 100 mL of absolute ethanol, and treated with 0.371 mL of 1 N HCl; the resulting mixture was degassed with nitrogen. Palladium on carbon (5%, 100 mg) was added and the mixture stirred under an atmosphere of hydrogen gas using a balloon, at room temperature, for 4.2 hours. The resulting solution was filtered through celite, the residue was washed well with ethanol and the resulting filtrate was evaporated to give the title compound (172 mg) as a colorless foam.

E. $N^\alpha$-3-Indolecarbonyl-$N^\epsilon$-(4-(1-Maleimido)hexanoyl))-L-Lysyl-L-Phenylalanine N-(Methyl)Benzylamide: CP-0533 (hydrochloride salt, 140 mg, 0.245 mmole), 4-(1-maleimido)-butanoic acid (45 mg, 0.25 mmole), N,N-diisopropylethylamine (0.170 mL, 0.98 mmole) were dissolved in dichloromethane (5 mL). BOP reagent (107 mg, 0.250 mmole) was added and the reaction stirred under nitrogen at room temperature for 3.5 hours. The reaction mixture was then diluted with dichloromethane and worked up according to general method A. The resulting foam was purified by chromatography on silica gel eluting with 2–8% MeOH in $CH_2Cl_2$ to yield 70 mg of the title compound as a colorless foam.

Compound 3: $N^\alpha$-3-Indolecarbonyl-$N^\epsilon$-(4-(1-maleimido)hexanoyl))-L-lysyl-L-phenylalanine N-(methyl)benzylamide (10 mg, 14 mmole) was treated with 1 mL of dimethylformamide to which was added approximately 100 mL of a 100 mMolar solution of ammonium bicarbonate in water. CP-0126 [Cheronis et al, J. Med. Chem. 35:1563 (1992)] (tetra trifluroacetate salt, 24 mg, ~14 mmole) was added. The reaction was then stirred one hour at room temperature under nitrogen. The mixture was purified by preparative C-18 HPLC (25×300 mm column) using a gradient of 10–85% $CH_3CN$ (0.1% TFA) over 60 minutes. Flow rate of 10 mL/min. Lyophilization of appropriate fractions provided 22 mg of the title compound as a colorless lyophilate. C18-HPLC 25–85% $CH_3CN$ (0.1% TFA), over 40 minutes. Retention time 15.3 minutes. FAB-MS Calculated 1969 Found 1970 (M+H).

EXAMPLE IV—Synthesis of Compound 4

A. tert-Butyloxycarbonyl-L-3-(2-Napthyl)-Alanine N-(Methyl)- Benzylamide: tert-Butyloxycarbonyl-L-3-(2-napthyl)-alanine (2.21 g, 7.0 mmole), N-(methyl)-benzylamine (0.86 mL, 6.67 mmole), diisopropylethylamine (3.0 mL) were dissolved in 50 mL of dichloromethane and chilled to 0° C. under nitrogen. Bis (2-oxo-3-oxazolidinyl)phosphinic chloride ( 2.04 g, 8.00 mmole) was added and the reaction stirred at 0° to 5° C. for approximately 15 hours. The reaction mixture was diluted with dichloromethane and worked up according to method A. The resulting foam was purified by chromatography on silica gel eluting with 50% acetone in hexanes. Pooling of appropriate fractions, removal of solvent and drying under high vacuum provided the title compound (2.48 g) as a colorless foam.

B. L-3- (2-Napthyl) -Alanine N-(Methyl) Benzylamide: tert-Butyl- oxycarbonyl-L-3-(2-napthyl)-alanine N-(methyl)benzylamide (2.48 g) was deblocked according to general method B, to yield the title compound (1.68 g) as an oil.

C. $N^\alpha$-tert-Butyloxycarbonyl-$N^\epsilon$-Benzyloxycarbonyl-L-Lysyl-L-3-(2-Napthyl)-Alanine N(Methyl) Benzylamide: $N^\alpha$-tert-Butyloxycarbonyl-$N^\epsilon$-benzyloxycarbonyl-L-Lysine (1.05 g, 2.76 mmole) was coupled to L-3-(2-napthyl)-alanine N-(methyl) benzylamide (837 mg, 2.63 mmole) by general method C. Extractive work up according to general method A, provided the title compound (1.68 g) as a colorless foam of sufficient purity for synthetic purposes.

D. $N^\epsilon$-Benzyloxycarbonyl-L-Lysyl-L-3-(2-Napthyl)-Alanine N-(Methyl)Benzylamide: $N^\alpha$-tert-Butyloxycarbonyl-$N^\epsilon$-benzyloxycarbonyl-L-lysyl-L-3-(2-napthyl)-alanine N-(methyl) benzylamide (1.65 g) was deblocked by method B to yield the title compound (1.02 g) as an oil.

E. $N^\alpha$-3-Indolecarbonyl-$N^\epsilon$-Benzyloxycarbonyl-L-Lysyl-L-3-(2-Napthyl)-Alanine N(Methyl)Benzylamide: 3-Indolecarboxylic acid (284 mg, 1.76mmole),$N^\epsilon$-benzyloxycarbonyl-L-lysyl-L-3-(2-napthyl)-alanine N-(methyl)benzylamide (1.02 g, 1.76 mmole), and diisopropyl- ethylamine (0.981 mL, 5.63 mmole) were dissolved in 20 mL of dichloromethane, and treated with BOP (779 mg, 1.76 mmole). An additional 0.5 equivalents of 3-indolecarboxylic acid, BOP, and 3 equivalents of DIEA were added after 2 hours. After three additional hours the reaction was worked up according to general method A. Silica gel chromatography eluting with 45 to 75% acetone in hexanes, provided 1.10 g of the title compound as a colorless foam.

F. (CP-0535 Hydrochloride Salt): $N^\alpha$-3-Indolecarbonyl-$N^\epsilon$-Benzyloxycarbonyl-L-Lysyl-L-3-(2-Napthyl)-Alanine N-(Methyl)Benzyl- amide (1.1 g) was dissolved in 100 mL of absolute ethanol, and treated with 1.5 mL of 1 N HCl; the resulting mixture was degassed with nitrogen. Palladium on carbon (5%, 1.0 g) was added and the mixture stirred under an atmosphere of hydrogen gas using a balloon, at room temperature, for approximately 3 hours. An additional gram of catalyst was added and the reaction stirred an additional 15 hours. The resulting solution was filtered through celite, the residue was washed well with ethanol and the resulting filtrate was evaporated to give the title compound (562 mg) as a colorless foam.

G. $N^\alpha$-3-Indolecarbonyl-$N^\epsilon$-(4-(1-Maleimido)hexanoyl))-L-Lysyl-L-3-(2-Napthyl)-Alanine N-(Methyl)Benzylamide: CP-0535 (hydrochloride salt, 560 mg, 0.90 mmole), 4-(1-maleimido)-butanoic acid (164 mg), N,N-diisopropylethylamine (0.624 mL) were dissolved in dichloro- methane (10 mL). BOP reagent (396) was added and the reaction stirred under nitrogen at room temperature for two hours. The reaction mixture was then diluted with dichloromethane and worked up according to general method A. A portion of the resulting foam was purified by chromatography on silica gel eluting with 2–8% MeOH in $CH_2Cl_2$ to yield 195 mg of the title compound as a colorless foam.

Compound 4: $N^\alpha$-3-Indolecarbonyl-$N^\epsilon$-(4-(1-maleimido)hexanol))-L-lysyl-L-3-(2-napthyl)-alanine N-(methyl)benzylamide (32 mg) was treated with 1 mL of dimethylformamide to which was added 400 mL of a 100 mMolar solution of ammonium bicarbonate in water. CP-0126 [Cheronis et al, *J. Med. Chem.* 35:1563 (1992)] (tetra trifluro- acetate salt, 73 mg) was added. The reaction was then stirred 3 hours at room temperature under nitrogen. The mixture was purified by preparative C-18 HPLC (25×300 mm column) using a gradient of 10–85 % $CH_3CN$ (0.1% TFA) over forty minutes. Flow rate of 10 mL/min. Lyophilization of appropriate fractions provided 50 mg of the title compound as a colorless lyophilate. C18-HPLC 25–85% $CH_3CN$ (0.1% TFA), over 40 minutes. Retention time 17.1 minutes. LD-MS Calculated 2019 Found 2021 (M+H). AAA Gly 1.00 (1), Arg 3.52 (3) [artificially high due to break down products from 3-indole carboxylic acid], Pro 0.93 (1), Leu 0.86 (1), Phe 1.89 (2), Lys 0.85 (1), Hyp 0.90 (1), derivatives of Cys and 2-Nal were observed qualitatively.

EXAMPLE V—Synthesis of Control Analogs

The following are examples of the synthesis of control analogs which exhibit only $NK_1$ receptor antagonist activity.

CP-0528: 6-(1-Maleimido)-hexanoyl-L-threonyl-$N^{Im}$-formyl-D-tryptophanyl-L-phenylalanine N-(methyl)-benzylamide (35 mg) was treated with 2-mercaptoethanol as described below for CP-0529. The reaction product was purified by preparative C-18 HPLC (25×300 mm column) using a gradient of 10–85% $CH_3CN$ (0.1% TFA) over 60 minutes. Flow rate of 10 mL/min. Lyophilization of appropriate fractions provided 18 mg of the title compound as a colorless lyophilate. C18-HPLC 25–85% $CH_3CN$ (0.1% TFA), over 40 minutes. Retention time 17.4 minutes. FAB-MS Calculated 854 Found 855 (M+H).

CP-0529: 4-(1-Maleimido)-butanoyl-L-threonyl-$N^{Im}$-formyl-D-tryptophanyl-L-phenylalanine N-(methyl)-benzylamide (34 mg, 45 mmole) was dissolved in 1 mL of dimethylformamide and treated with 32 mL of 2-mercaptoethanol, followed by approximately 100 mL of a 100 mMolar solution of ammonium bicarbonate. The reaction stirred under nitrogen for 2.5 hours. The reaction product was purified by preparative C-18 HPLC (25×300 mm column) using a gradient of 5–85% $CH_3CN$ (0.1% TFA) over 60 minutes. Flow rate of 10 mL/min. Lyophilization of appropriate fractions provided 4 mg of the title compound as a colorless lyophilate. C18-HPLC 25–85% $CH_3CN$ (0.1% TFA), over 40 minutes. Retention time 16.5 minutes. LD-MS Calculated 827 (M+H) Found 827 (M+H).

CP-0580: $N^\alpha$-3-Indolecarbonyl-$N^\epsilon$-(4-(1-maleimido)hexanoyl))-L-lysyl-L-3-(2-n apthyl)alanine N-(methyl)benzylamide (38 mg, 50 mmole) was reacted with 2-mercaptoethanol as described for CP-0529. The reaction was stirred under nitrogen for 3 hours. The reaction product was purified by preparative C-18 HPLC (25×300 mm column) using a gradient of 10–85% $CH_3CN$ (0.1% TFA) over 40 minutes. Flow rate of 10 mL/min. Lyophilization of appropriate fractions provided 20 mg of the title compound as a colorless lyophilate. C18-HPLC 25–85% $CH_3CN$ (0.1% TFA), over 40 minutes. Retention time 18.8 minutes. FAB-MS Calculated 832 Found 833 (M+H).

EXAMPLE VI—General synthetic chemical procedures

The following are general synthetic chemical procedures referenced in the description of the synthesis of the examples.

General Method A—General Work-Up: The reaction mixture was diluted with approximately 5 volumes of the solvent used for the reaction (methylene chloride or ethyl acetate). The resulting mixture was washed twice with 5% potassium hydrogen sulfate solution, twice with saturated sodium bicarbonate solution, and once with saturated sodium chloride solution. Unless described differently, the solution was dried over anhydrous sodium sulfate, filtered and the solvent removed by rotary evaporation. Traces of residual solvent were removed by drying under high vacuum.

General Method B—Trifluroacetic Acid Mediated Deprotection: The $N^\alpha$-t-Boc-Amino acid or peptide was dissolved in dichloromethane (~10 mL/mmole of amino acid) and treated with trifluoroacetic acid (2.5 mL/mmole) at 0° C. The progress of the deprotection reaction was monitored by thin layer chromatography. After the reaction had reached completion (2–6 hours), the reaction mixture was diluted with dichloromethane and carefully washed repeatedly with saturated sodium bicarbonate solution. The mixture was then washed repeatedly with sodium chloride solution and the resulting organic solution was dried over anhydrous sodium sulfate and concentrated in vacuo.

General Method C—EDC/HOBt Peptide Coupling: The $N^\alpha$-t-Boc-amino acid or carboxylic acid (1.1 equivalent) was dissolved in dimethylformamide (10 mL/mmole), treated with 1-hydroxybenzotriazolhydrate (2.4 equivalents) and chilled to 0° C. EDC [1-(3-diaminopropyl)-3-ethylcarbodiimide hydrochloride, 1.05 equivalents] was added and the reaction was allowed to stir for approximately one hour at 0° C. under nitrogen atmosphere. The amine component (1.0 equivalent) was then added and the stirred mixture was allowed to warm to room temperature. The reaction was monitored for completion by thin layer chromatography.

EXAMPLE VII—In vitro $B_2$ Antagonist Activity Measurements

The standard rat uterus $pA_2$ assay was conducted as follows: Female Sprague-Dawley rats (200–250 g) were pretreated with stilbesterol (100 ug/kg) and killed 18 hours later by a blow on the head and exsanguinated. Uterine horns were removed, placed under a 1 g resting tension in 4 mL tissue baths containing De Jalon's solution at 31° C. and aerated. Concentration-effect curves were constructed for bradykinin in the absence and presence of antagonist (pre-incubated for 15 minutes). Antagonist potency was calculated according to the method of Arunlakshana et al. (*Br. J. Pharmacol.* 14: 48–58 (1959)). Following exposure to the highest concentration of antagonist (usually $10^{-5}$ molar) each tissue was washed at 10 minute intervals for 40 minutes, after which time a concentration-effect curve was again constructed for bradykinin. The $pD_2$ (-log[molar concentration producing 50% of the maximum original response to bradykinin]) for bradykinin at this time was calculated and compared to the $pD_2$ of the initial control concentration-effect curve for bradykinin. The difference in $pD_2$ values compared to concurrent control reflected the "percentage recovery" of agonist response.

EXAMPLE VIII—In vitro $NK_1$ Antagonist Activity Measurements

Guinea pig ileum tissues were used to assay the neurokinin-1 antagonist activity of the compounds. Segments of ileum were placed under a resting tension of 2 g in 4 ml tissue baths containing Kreb's solution containing 100 ng/mL atropine at 37° C., aerated with 95% $O_2$/ 5% $CO_2$. Concentration/effect curves were constructed as described above using substance P-o-methyl ester as the agonist.

TABLE 1

In Vitro Activity of Compounds Acting as Antagonists on Bradykinin ($BK_2$, rat uterus) or Neurokinin ($NK_1$, guinea pig ileum) Receptors. (Antagonist activity is reported as $pA_2$ value.)

| Compound Number | $NK_1$ $pA_2$ (% recovery) | $BK_2$ $pA_2$ (% Recovery) |
| --- | --- | --- |
| CP-0126 | | 7.1 (100%) n = 5 |
| FR113680 | 7.0 (53%) n = 5 | |
| CP-0528 | 6.5 (80%) n = 5 | |
| Compound 1 | 7.3 (0%) n = 6 | 8.0 (20%) n = 4 |
| CP-0529 | 6.9 (55%) n = 6 | |
| Compound 2 | 6.9 (48%) n = 3 | 8.2 (20%) n = 6 |
| CP-0533 | 6.3 (73%) n = 6 | |
| Compound 3 | 6.9 (53%) | 7.3 (29%) n = 6 |
| CP-0535 | 7.5 (41%) n = 5 | |
| CP-580 | 8.0 (4%) n = 4 | |
| Compound 4 | 9.0 (12%) n = 5 | 7.3 (6%) n = 4 |

EXAMPLE IX—Stability Studies

Plasma samples were prepared by collection of whole blood from healthy male and female human volunteers or guinea pigs. Samples were collected into culture tubes containing sodium heparin, and were then spun at 4° C. at 2000 rpm for ten minutes. Supernatant fractions were removed by aspiration and stored in vials at −20° C. Rat or porcine lung and kidney cortical membranes were prepared using differential centrifugation. Membrane preparations were stored at −20° C. The test compound was diluted to 1 mM concentration in PBS (0.0132 M phosphate, 0.1454 M NaCl, pH 7.2). Ten microliters of this working solution were delivered into a series of Eppendorf tubes, followed by human or guinea pig plasma (90 uL) or PBS as a control blank, and incubated for various time periods. At each time point the reaction was quenched with the addition of 100 uL 1N HCl in either acetonitrile or ethanol. Samples were allowed to stand approximately fifteen minutes and were then spun at 14,000 rpm for 10 minutes. Supernatant fractions were removed, filtered through 0.22 uM filters (Millipore) and analyzed by HPLC (C18, 12–80% acetonitrile in water, both containing 0.1% trifluoroacetic acid, monitoring at 214 nm.

Porcine kidney preparations were diluted 1:10 with PBS; rat kidney preparations were diluted 1:100 with PBS. The test compound solutions (10 uL) were added to a series of Eppendorf tubes, followed by the respective diluted membrane preparations (90 uL). At various time points the reactions were quenched by the addition of 100 uL of ethanol, centrifuged and analyzed by HPLC as described above. The half-life for the disappearance of the HPLC peak was determined using the computer program ENZFIT (Elsevier). Stability data are given in Table 2. CP-0127 is a dimer disclosed in Example 1 of application Ser. No. 07/859,582, continuation parent of application Ser. No. 08/440,352, of the formula:

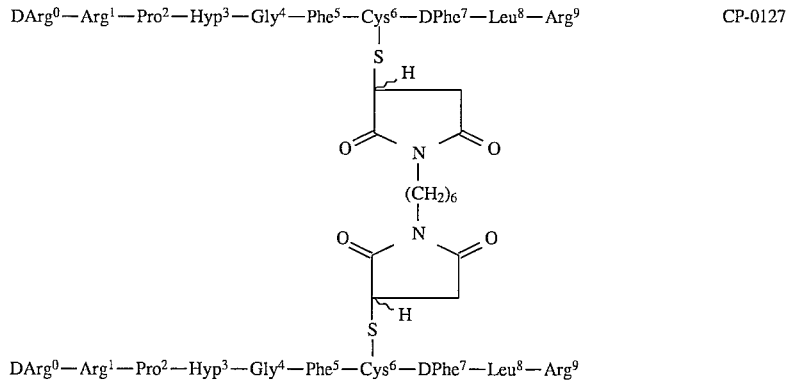

DArg⁰—Arg¹—Pro²—Hyp³—Gly⁴—Phe⁵—Cys⁶—DPhe⁷—Leu⁸—Arg⁹      CP-0127

DArg⁰—Arg¹—Pro²—Hyp³—Gly⁴—Phe⁵—Cys⁶—DPhe⁷—Leu⁸—Arg⁹

The compound itself is a highly active bradykinin antagonist.

TABLE 2

In Vitro Stability Studies. (Half-life measured in hours.)

|  | Bradykinin | CP-0127 | Compound 4 |
|---|---|---|---|
| Human Plasma | 0.45 | 2.75 | >6 |
| Guinea Pig Plasma | — | — | >6 |
| Rat Kidney | 0.13 | 0.66 | >6 |
| Pig Kidney | 0.05 | >6 | >6 |

EXAMPLE X—Effect of Compound 4 on Kinin-Induced Lung Resistance Changes in the Anesthetized, Mechanically-Ventilated Guinea Pig Male guinea pigs (300–500 g) were anesthetized with urethane (2 mg/kg, ip). Following cannulation of a carotid artery, jugular vein, and the trachea, the animal was placed in a whole body plethysmograph and lung resistance and compliance were monitored. All animals received atropine (1 mg/kg, iv), propranolol (1mg/kg, iv), captopril (1 mg/kg, iv), and phosphoramidon (0.1 mg/kg, iv) prior to antagonist infusion. Compound 4 was infused for 15 min prior to initiation of a intravenous bradykinin (0.01–100 ug/kg) or substance P-O-methyl ester (1–30 ug/kg) dose-response curve. Compound 4 inhibited both bradykinin- (1 ug/kg bolus) and substance P methyl ester (30 ug/kg bolus) induced increases in lung resistance (indicative of airway constriction) with $ED_{50}$s of 30 ug/kg/min and 2 ug/kg/min, respectively.

What is claimed is:

1. A compound of the formula:

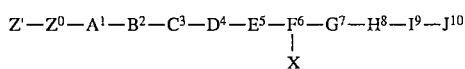

wherein:
$Z'-Z^0-A^1-B^2-C^3-D^4-E^5-F^6-G^7-H^8-I^9-J^{10}$
is a peptide antagonist of bradykinin;
where
   $Z'$ is optional but, if present, is hydrogen, acetyl, adamantylcarboxyl, or adamantylacetyl;
   $Z^0$ is optional but, if present, is D or L arginine, D or L lysine or D or L ornithine;
   $A^1$ is D or L arginine, D or L lysine or D or L ornithine;
   $B^2$ is proline, hydroxyproline, serine, threonine, N-methyl serine or N-methyl threonine;
   $C^3$ is proline or hydroxyproline;
   $D^4$ is glycine or alanine;
   $E^5$ is phenylalanine, 2-indaneglycine or 2-thienylalanine;
   $F^6$ is cysteine, homocysteine, penicillamine or β-methylcysteine;
   $G^7$ is D-Tic, D-phenylalanine, 2-indaneglycine, D-cyclopentylglycine or D-cyclohexylglycine;
   $H^8$ is phenylalanine, leucine, Oic, norvaline or glycine substituted at the N atom with a cyclopentyl, cyclohexyl or phenyl group;
   $I^9$ is OH, arginine or lysine;
   $J^{10}$ is optional but, if present, is OH; and
   X is

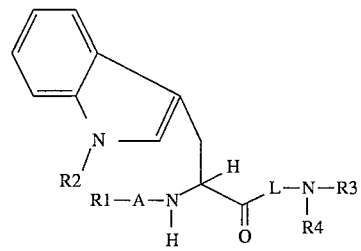

(I)

wherein
   R1 is $-Z-(CH_2)_m-CO-$
   where Z is a succinimido, phenyl or pyrrolidinone group where the sulfur atom of $F^6$ is attached to Z directly or via $(CH_2)$, and m is an integer from 1 to 8;
   A is threonine;
   L is phenylalanine;
   R2 is H or $C_1-C_8$ alkyl;
   R3 is $C_1-C_8$ alkyl; and
   R4 is benzyl; or
   X is

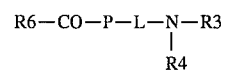

(II)

where R6 is

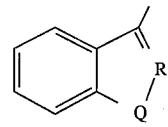

where R is N or CH; and
   Q is NH;
   P is

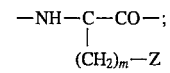

(III)

wherein m is 1 to 8 and Z is a succinimido, phenyl or pyrrolidinone group optionally substituted with $(C_1-C_8)$ alkylamide where the sulfur atom of $F^6$ is attached to Z directly or via $(CH_2)$; and
   L is phenylalanine, tyrosine, 3-(2-naphthyl)-alanine, 2-indaneglycine or Tic;
   R3 is $C_1-C_8$ alkyl; and
   R4 is benzyl;
   where said compound is an antagonist of bradykinin receptors and neurokinin 1 receptors.

2. The compound according to claim 1 wherein X is formula II.

3. The compound of claim 2 wherein m is 4 and L is Nal.

4. The compound of claim 1, wherein Z is a succinimido group.

5. The compound according to claim 1 wherein $G^7$ is D-phenylalanine.

6. The compound according to claim 1 wherein $I^9$ is arginine.

7. A pharmaceutical composition comprising the compound according to claim 1 and a pharmaceutically acceptable carrier.

8. A method of treating pain or inflammation comprising administering the compound according to claim 1 to a subject in need of such treatment.

9. A method of treating asthma or bronchitis comprising administering the compound according to claim 1 to a subject in need of such treatment.

10. The compound of claim 1 wherein $H^8$ is phenylalanine or Oic.

* * * * *